US011306312B2

(12) United States Patent
Wickstrom et al.

(10) Patent No.: US 11,306,312 B2
(45) Date of Patent: Apr. 19, 2022

(54) **COMPOSITIONS AND METHODS FOR *MYC* MESSENGER RNA INHIBITORS**

(71) Applicants: THOMAS JEFFERSON UNIVERSITY, Philadelphia, PA (US); BOUND THERAPEUTICS, LLC, Marlton, NJ (US)

(72) Inventors: Eric Wickstrom, Philadelphia, PA (US); Yuan-Yuan Jin, Marlton, NJ (US)

(73) Assignees: Thomas Jefferson University, Philadelphia, PA (US); Bound Therapeutics, LLC, Marlton, NJ (US)

( * ) Notice: Subject to any disclaimer, the term of this patent is extended or adjusted under 35 U.S.C. 154(b) by 92 days.

(21) Appl. No.: 16/643,820

(22) PCT Filed: Aug. 31, 2018

(86) PCT No.: PCT/US2018/049055
§ 371 (c)(1),
(2) Date: Mar. 2, 2020

(87) PCT Pub. No.: WO2019/046698
PCT Pub. Date: Mar. 7, 2019

(65) Prior Publication Data
US 2020/0208151 A1    Jul. 2, 2020

Related U.S. Application Data

(60) Provisional application No. 62/553,471, filed on Sep. 1, 2017.

(51) Int. Cl.
*C12N 15/11* (2006.01)
*C12N 15/113* (2010.01)
*A61K 47/62* (2017.01)
*A61K 48/00* (2006.01)

(52) U.S. Cl.
CPC ............ *C12N 15/113* (2013.01); *A61K 47/62* (2017.08); *A61K 48/00* (2013.01); *C12N 2310/11* (2013.01); *C12N 2320/30* (2013.01)

(58) Field of Classification Search
CPC .............. C12N 15/113; C12N 2310/11; C12N 2310/341; C12N 15/111; C12N 2310/00
See application file for complete search history.

(56) References Cited

U.S. PATENT DOCUMENTS

| 5,539,082 | A | 7/1996 | Nielsen et al. |
| 5,672,695 | A | 9/1997 | Eckstein et al. |
| 5,684,143 | A | 11/1997 | Gryaznov et al. |
| 5,858,988 | A | 1/1999 | Wang |
| 5,859,231 | A | 1/1999 | Shaw et al. |
| 6,248,878 | B1 | 6/2001 | Matulic-Adamic et al. |
| 6,291,438 | B1 | 9/2001 | Wang |
| 2004/0203145 | A1 | 10/2004 | Zamore et al. |
| 2005/0287151 | A1 | 12/2005 | Glass |
| 2009/0047295 | A1 | 2/2009 | Berry et al. |
| 2010/0249211 | A1 | 9/2010 | Prakash et al. |

FOREIGN PATENT DOCUMENTS

| WO | 9207065 A1 | 4/1992 |
| WO | 9315187 A1 | 8/1993 |

OTHER PUBLICATIONS

Vickers et al., Efficient reduction of target RNAs by small interfering RNAand RNase H-dependent antisense agents, JBC, vol. 278, pp. 7108-7118. (Year: 2003).*
De Santi et al., Human IGF1 pro-forms induce breast cancer cell proliferation via the IGF1 receptor, Cellular Oncology, vol. 39, pp. 149-159. (Year: 2016).*
Gao et al., Blockade of CD47 ameliorates autoimmune inflammation in CNS by suppressing IL-1-triggered infiltration of pathogenic Th17 cells, Journal of Autoimmunity, vol. 69, pp. 74-85. (Year: 2016).*
International Search Report and Written Opinion dated Nov. 20, 2018 for International Application No. PCT/US2018/049055.
Amarzguioui, et al., Nucleic Acids Research, vol. 31, Issue 2, Jan. 15, 2003, 589-595.
Bacon, et al., "Daily addition of an anti-c-MYC DNA oligomer induces granulocytic differentiation of human promyelocytic leukemia HL-60 cells in both serum-containing and serum-free media", Oncogene Research, 6(1), 1991, 21-32.
Bacon, et al., "Walking along human c-MYCmRNA with antisense oligodeoxynucleotides: maximum efficacy at the 5' cap region", Oncogene Research, 6(1), 1991, 13-19.
Barret, et al., "Genomic Amplification of 9p24.1 Targeting JAK2, PD-L 1, and PD-L2 is Enriched in'High-Risk Triple N'egative Breast Cancer", Oncotarget, vol. 6, No. 28, Sep. 22, 2015, 26483-26493.
Basu, et al., "Synthesis and characterization of a peptide nucleic acid conjugated to a D-peptide analog of insulin-like growth factor 1 for increased cellular uptake", Bioconjug Chem. 8(4), 1997, 481-488.
Burgin, et al., Biochemistry, 35, 1996, 14090.
Casey, et al., "MYC Regulates the Anti-Tumor Immune Response through CD47 and PD-L1", Science, vol. 352, Apr. 8, 2016, 227-231.
Eckstein, Antisense Nucleic Acid Drug Dev., 10(2), 2000, 117-21.
Hall, et al., Nucleic Acids Research, vol. 32, No. 20, 2004, 5991-6000.
Hall, et al., Nucleic Acids Research, vol. 34, Issue 9, May 1, 2006, 2773-2781.
Hann, et al., "A non-AUG translational initiation in c-myc exon 1 generates an N-terminally distinct protein whose synthesis is disrupted in Burkitt's lymphomas", Cell, 52(2), 1988, 185-195.
Herdewijn, et al., Antisense Nucleic Acid Drug Dev., 10(4), 2000, 297-310.

(Continued)

*Primary Examiner* — Dana H Shin
(74) *Attorney, Agent, or Firm* — Saul Ewing Arnstein & Lehr LLP; Kathryn Doyle; Justin Crotty

(57) ABSTRACT

The present invention provides compositions and methods of making and using MYC mRNA antisense inhibitors. In a particular embodiment, the invention features compositions and methods useful for the treatment of a condition (e.g., cancer).

21 Claims, 13 Drawing Sheets

Specification includes a Sequence Listing.

(56) References Cited

OTHER PUBLICATIONS

Hogg, et al., "BET-Bromodomain Inhibitors Engage the Host Immune System and Regulate Expression of the Immune Checkpoint Ligand PD-L1", Cell Reports, vol. 18, No. 9, Feb. 28, 2017, 2162-2174.
Huang, et al., "Prevention of tumor formation in a mouse model of Burkitt's lymphoma by 6 weeks of treatment with anti-c-myc DNA phosphorothioate", Molecular Medicine, 1(6), 1995, 647-658.
Limbach, et al., Nucleic Acids Res., 22, 1994, 2183.
Mangos, et al., J Am Chem Soc, 125(3), PMID: 12526664, 2003, 654-61.
Nielsen, et al., Science, 254(5037), 1991, 1497-1500.
Prakash, et al., "Antisense Oligonucleotides Containing Conformationally Constrained 2',4'-(N-Methoxy) aminomethylene and 2',4'-aminooxymethylene and 2'-O,4'-C-Aminomethylene Bridged Nucleoside Analogues Show mproved Potency in Animal Models", J Med Chem, vol. 53, pp. 1636-1650, Feb. 25, 2010, 1636-1650.
Rahman, et al., "Design, synthesis, and properties of 2',4'-BNA(NC): a bridged nucleic acid analogue", J Am Chem Soc 130(14), 2008, 4886-4896.
Rusckowski, et al., Antisense Nucleic Acid Drug Dev., 10(5), 2000, 333-15.
Smith, et al., "Antisense c-myc and immunostimulatory oligonucleotide inhibition of tumorigenesis in a murine B-cell lymphoma transplant model", Journal of the National Cancer Institute, 90(15), 1998, 1146-1154.
Sonar, et al., "Fluorescence Detection of KRAS2 mRNA Hybridization in Lung Cancer Cells with PNA-Peptides Containing an Internal Thiazole Orange", Bioconjugate Chem, vol. 25, Iss. 9, Aug. 19, 2014, 1697-1708.
Stein, et al., J. Clin Invest., 108(5), 2001, 641-4.
Uhlman, et al., Chem. Rev., 90(4), 1990, 543-584.
Usman, et al., CurrOpin Struct Biol., 6(4), Aug. 1996, 527-33.
Vorobjev, et al., Antisense Nucleic Acid Drug Dev., 11(2), 2001, 77-85.
Wickstrom, "Anti-c-MYCDNA increases differentiation and decreases colony formation by HL-60 cells", In Vitro Cellular & Developmental Biology 25(3 Pt 1), 1989, 297-302.
Wickstrom, et al., "Down-regulation of c-Myc antigen expression in lymphocytes of Eµ-c-myc transgenic mice treated with anti-c-myc DNA methylphosphonates", Cancer Research 52(24), 1992, 6741-6745.
Wickstrom, et al., "Human promyelocytic leukemia HL-60 cell proliferation and c-Myc protein expression are inhibited by an antisense pentadecadeoxynucleotide targeted against c-MYC mRNA", Proceedings of the National Academy of Sciences USA 85(4), 1988, 1028-1032.
Wirth, et al., "Concepts to Target MYC in Pancreatic Cancer", Mol Cancer Ther 15(8), 2016, 1792-1798.

\* cited by examiner

```
                        SEQUENCE LISTING

<160> NUMBER OF SEQ ID NOS: 4

<210> SEQ ID NO 1
<211> LENGTH: 15
<212> TYPE: RNA
<213> ORGANISM: Artificial Sequence
<220> FEATURE:
<223> OTHER INFORMATION: A sequence was chosen corresponding to the 5'
      end of the secondary, shorter transcript of MYC mRNA (Hann et al.
      Cell 52.2 (1988): 185-195) at nt 170-184 of NCBI Reference
      Sequence NM_002467.4

<400> SEQUENCE: 1
uguaguaauu ccagc                                                    15

<210> SEQ ID NO 2
<211> LENGTH: 15
<212> TYPE: DNA
<213> ORGANISM: Artificial Sequence
<220> FEATURE:
<223> OTHER INFORMATION: Antisense sequence to SEQ ID NO: 1.

<400> SEQUENCE: 2
gctggaatta ctaca                                                    15

<210> SEQ ID NO 3
<211> LENGTH: 4
<212> TYPE: PRT
<213> ORGANISM: Artificial Sequence
<220> FEATURE:
<223> OTHER INFORMATION: tetrapeptide analog of insulin-like growth
      factor 1 (IGF1)

<400> SEQUENCE: 3

Cys Ser Leu Cys
1

<210> SEQ ID NO 4
<211> LENGTH: 4
<212> TYPE: PRT
<213> ORGANISM: Artificial Sequence
<220> FEATURE:
<223> OTHER INFORMATION: Spacer linking SEQ ID NO: 3 to Myc BNA

<400> SEQUENCE: 4

Ala Glu Glu Ala
1
```

COMPOSITIONS AND METHODS FOR *MYC* MESSENGER RNA INHIBITORS

CROSS REFERENCE TO RELATED APPLICATIONS

The present application is a national phase application under 35 U.S.C. 371 of International Application No. PCT/US2018/049055, filed Aug. 31, 2018, which claims priority under 35 U.S.C. § 119(e) to U.S. Provisional Application No. 62/553,471, filed Sep. 1, 2017, which are incorporated herein by reference in their entirety.

BACKGROUND OF THE INVENTION c-Myc is a transcription factor protein that regulates the expression of a multitude of gene products involved in cell proliferation, growth, differentiation, and apoptosis. The MYC gene is genetically activated and overexpressed in many human cancers and this overexpression has been causally linked to tumorigenesis. Work with inducible transgenic mouse models has shown that growth of MYC-induced tumors is dependent on continuous expression of c-Myc protein. For example, in the tetracycline-off mouse model (where MYC expression can be turned off by the addition of tetracycline or doxycycline), tumors grow only when MYC is "on," When MYC is turned "off," tumors regress. MYC inactivation in mouse models results in tumor regression through the induction of proliferative arrest and apoptosis.

The c-Myc protein has resisted effective drug development so far because it lacks druggable pockets found in enzyme active sites. To date, MYC messenger RNA (mRNA) antisense DNA analog knockdown agents have required impractically high blood concentrations, due to poor uptake of the DNA analogs. Synthetic RNA analogs are limited by nuclease attack, systemic distribution to all organs, slow uptake into cells, and slow trafficking inside cells. There is thus a need in the art for sophisticated design of nuclease-resistant antisense RNA analogs that target MYC mRNA, especially those coupled with peptide ligands that will direct the RNA analogs to particular cell surface receptors, mediate endocytosis primarily into diseased cells, and deliver the agents into the cytoplasm where mRNA functions. The present invention addresses and satisfies this need.

SUMMARY OF THE INVENTION

In one aspect, the invention provides an antisense 2'-O,4'-C-aminomethylene bridged nucleic acid-deoxyribonucleic acid-2'-O,4'-C-aminomethylene bridged nucleic acid chimera (BNA) capable of knocking down MYC activity, wherein the BNA comprises SEQ ID NO: 2.

In various embodiments, the BNA further comprises a conjugated peptide capable of directing endocytosis via the insulin-like growth factor 1 (IGF1) receptor.

In various embodiments, the peptide comprises SEQ ID NO: 3.

In one aspect, the invention provides a method of knocking down MYC mRNA translation in a cell, the method comprising contacting the cell with a BNA comprising SEQ ID NO: 2.

In various embodiments, knocking down MYC mRNA expression further comprises knocking down PD-L1 protein expression.

In various embodiments, the BNA further comprises a conjugated peptide capable of directing endocytosis via the insulin-like growth factor 1 (IGF1) receptor.

In various embodiments, the peptide comprises SEQ ID NO: 3.

In another aspect, the invention provides a method of treating a condition in a subject, the method comprising administering to the subject a therapeutically effective amount of a bridged nucleic acid (BNA) capable of knocking down MYC mRNA translation, wherein the BNA comprises SEQ ID NO: 2.

In various embodiments, knocking down MYC mRNA translation further comprises knocking down PD-L1 protein expression.

In various embodiments, wherein the BNA further comprises a conjugated peptide capable of directing endocytosis via the insulin-like growth factor 1 (IGF1) receptor.

In various embodiments, the peptide comprises SEQ ID NO: 3.

In various embodiments, the condition is cancer.

In various embodiments, the cancer is selected from the group consisting of breast cancer and lung cancer.

In various embodiments, the condition is selected from the group consisting of inflammation, arthritis, neurodegeneration, cardiovascular disease, and autoimmune disorders.

In another aspect, the invention provides a kit comprising a 2'-O,4'-C-aminomethylene bridged nucleic acid-deoxyribonucleic acid-2'-O,4'-C-aminomethylene bridged nucleic acid chimera (BNA) capable of knocking down MYC activity, wherein the BNA comprises SEQ ID NO: 2, and instructional material for use thereof.

In another aspect, the invention provides a pharmaceutical composition comprising the BNA and a pharmaceutically acceptable carrier.

In various embodiments knocking down MYC mRNA translation further comprises knocking down PD-L2, CD47, and Jak2 protein expression.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIG. 1A shows a Western blot of c-Myc and PD-L1 expression in MDA-MB-231 cells 48 hours post transfection of 50 nMMYC BNA. FIGS. 1B-1C show Western blot quantification of FIG. 1A.

DETAILED DESCRIPTION OF THE INVENTION

Definitions

Figure 1A:
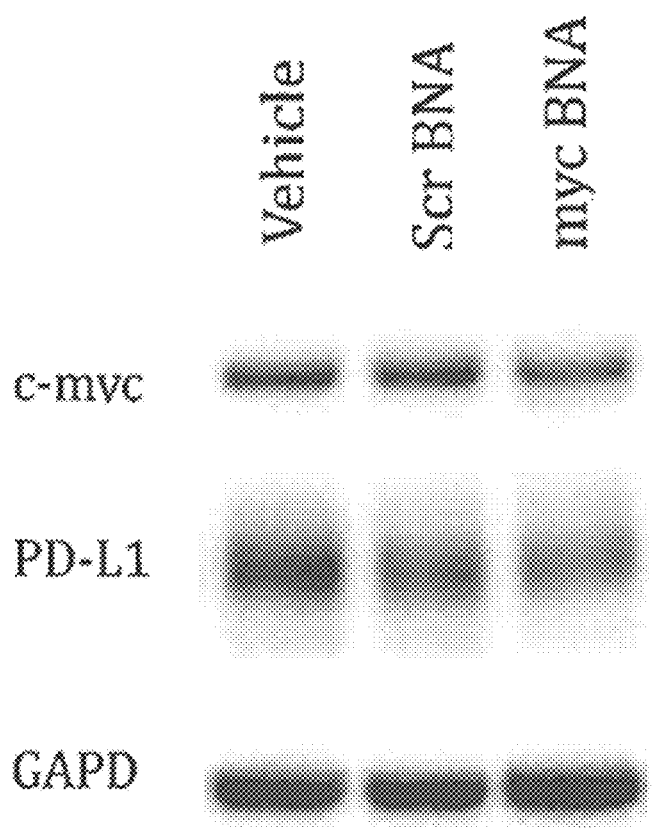
FIGS. 1A-1C are a series of graphs and images illustrating the finding that transfection of 50 nM MYC NC-BNA-DNA-NC-BNA gapmer (BNA) in MDA-MB-231 cells lowered c-Myc and PD-L1 protein expression.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used. It is also to be understood that the terminology used herein is for the purpose of describing particular embodiments only, and is not intended to be limiting.

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, analytical chemistry, immunology, and nucleic acid chemistry and hybridization are those well-known and commonly employed in the art. Standard techniques or modifications thereof are used for chemical syntheses and chemical analyses.

The articles "a" and "an" are used herein to refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a concentration, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "affinity" for a molecule towards another refers to the degree (or tightness) of binding between the two molecules. A higher affinity means tighter binding between the two molecules. Affinity can be quantified in terms of dissociation constant (or $K_d$), where a $K_d$ value that is lower in magnitude (closer to zero) indicates a higher affinity.

An "amino acid" as used herein is meant to include both natural and synthetic amino acids, and both D and L amino acids. "Standard amino acid" means any of the twenty L-amino acids commonly found in naturally occurring peptides. "Nonstandard amino acid residues" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides, and particularly at the carboxy- or amino-terminus, can be modified by methylation, amidation, acetylation or substitution with other chemical groups which can change a peptide's circulating half-life without adversely affecting activity of the peptide. Additionally, a disulfide linkage may be present or absent in the peptides.

As used herein, "bridged nucleic acid" or "BNA" refers to a modified nucleic acid in which the sugar conformation of the nucleotide is locked by bridging. Examples of bridged nucleic acids include but are not limited to 2'-O,4'-C-methylene bridged nucleic acid (LNA), ENA (NA-2), Aza-ENA (NA-3), NA-4, and 2',4'-BNA$^{COC}$. In one embodiment, the bridged nucleic acid is the NC-BNA analog (2'-O,4'-C-aminomethylene bridged nucleic acid).

"Effective amount" or "therapeutically effective amount" are used interchangeably herein, and refer to an amount of a compound, formulation, material, or composition, as described herein, effective to achieve a particular biological result. Such results may include, but are not limited to, treatment of a disease or condition as determined by any means suitable in the art.

The direction of 5' to 3' addition of nucleotides to nascent RNA transcripts is referred to as the transcription direction. The DNA strand having the same sequence as an mRNA is referred to as the "coding strand" or "sense strand"; sequences on the DNA strand which are located 5' to a reference point on the DNA are referred to as "upstream sequences"; sequences on the DNA strand which are 3' to a reference point on the DNA are referred to as "downstream sequences."

An "individual", "patient" or "subject", as that term is used herein, includes a member of any animal species including, but are not limited to, birds, humans and other primates, and other mammals including commercially relevant mammals such as cattle, pigs, horses, sheep, cats, and dogs. Preferably, the subject is a human.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

As used herein, the term "nucleic acid" refers to deoxyribonucleotides, ribonucleotides, or modified nucleotides, oligomers, and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid. Examples of such analogs include, without limitation, phosphorothioates, phosphoramidates, boranophosphates, methylphosphonates, 2-O-alkyl ribonucleotides, and peptide nucleic acids (PNAs).

As used herein, "nucleotide" is used as recognized in the art to include those with natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, e.g., Usman and McSwiggen, supra; Eckstein, et al., International PCT Publication No. WO 92/07065; Usman et al, International PCT Publication No. WO 93/15187; Uhlman & Peyman, supra, all are hereby incorporated by reference herein). There are several examples of modified nucleic acid bases known in the art as summarized by Limbach, et al, Nucleic Acids Res. 22:2183, 1994. Some of the non-limiting examples of base modifications that can be introduced into nucleic acid molecules include, hypoxanthine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin, et al., Biochemistry 35:14090, 1996; Uhlman & Peyman, supra). By "modified bases" in this aspect is meant nucleotide bases other than adenine, guanine, cytosine and uracil at 1' position or their equivalents.

As used herein, "modified nucleotide" refers to a nucleotide that has one or more modifications to the nucleoside, the nucleobase, pentose ring, or phosphate group. For example, modified nucleotides exclude ribonucleotides containing adenosine monophosphate, guanosine monophosphate, uridine monophosphate, and cytidine monophosphate and deoxyribonucleotides containing deoxyadenosine monophosphate, deoxyguanosine monophosphate, deoxythymidine monophosphate, and deoxycytidine monophosphate. Modifications include those naturally occuring that result from modification by enzymes that modify nucleotides, such as methyltransferases. Modified nucleotides also include synthetic or non-naturally occurring nucleotides. Synthetic or non-naturally occurring modifications in nucleotides include those with 2' modifications, e.g., 2'-methoxyethoxy, 2'-fluoro, 2'-thio, 2'-allyl, 2'-O-[2-(methylamino)-2-oxoethyl], 4'-thio, 4'-CH$_2$—O-2'-bridge, 4'-(CH$_2$)$_2$—O-2'-bridge, 2'-LNA, and 2'-O—(N-methylcarbamate) or those comprising base analogs. In connection with 2'-modified nucleotides as described for the present disclosure, by "amino" is meant 2'-NH$_2$ or 2'-O—NH$_2$, which can be modified or unmodified. Such modified groups are described, e.g., in Eckstein et al., U.S. Pat. No. 5,672,695 and Matulic-Adamic et al., U.S. Pat. No. 6,248,878.

As used herein, the term MYC activity means transcription of MYC and/or translation of c-Myc.

The term "oligonucleotide" typically refers to short polynucleotides, generally no greater than about 60 nucleotides. It will be understood that when a nucleotide sequence is represented by a DNA sequence (i.e., A, T, G, C and optionally, modified bases), this also includes an RNA sequence (i.e., A, U, G, C and optionally, modified bases) in which "U" replaces "T."

As used herein, the term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutical composition" or "pharmaceutically acceptable composition" refers to a mixture of at least one compound or molecule useful within the invention with a pharmaceutically acceptable carrier. The pharmaceutical composition facilitates administration of the compound or molecule to a patient. Multiple techniques of administering a compound or molecule exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "protein", "peptide" and "polypeptide" are used interchangeably, and refer to a compound comprised of amino acid residues covalently linked by peptide bonds. The term "peptide bond" means a covalent amide linkage formed by loss of a molecule of water between the carboxyl group of one amino acid and the amino group of a second amino acid. A protein or peptide must contain at least two amino acids, and no limitation is placed on the maximum number of amino acids that may comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Proteins" include, for example, biologically active fragments, substantially homologous proteins, oligopeptides, homodimers, heterodimers, variants of proteins, modified proteins, derivatives, analogs, and fusion proteins, among others. The proteins include natural proteins, recombinant proteins, synthetic proteins, or a combination thereof. A protein may be a receptor or a non-receptor.

The term to "treat," as used herein, means reducing the frequency with which symptoms are experienced by a subject or administering an agent or compound to reduce the frequency and/or severity with which symptoms are experienced. As used herein, "alleviate" is used interchangeably with the term "treat."

As used herein, "treating a disease, disorder or condition" means reducing the frequency or severity with which a symptom of the disease, disorder or condition is experienced by a subject. Treating a disease, disorder or condition may or may not include complete eradication or elimination of the symptom.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention includes the design and synthesis of novel precision medicine MYC-directed molecular therapeutic agents. In certain embodiments, the invention includes bridged nucleic acids (2'-O,4'-C-aminomethylene-BNAs; "NC-BNA") capable of knocking down MYC activity. In other embodiments, the invention includes treating a condition in a subject by administering a therapeutically effective amount of a BNA capable of knocking down MYC activity.

c-Myc is a transcription factor that regulates the expression of a multitude of gene products involved in cell proliferation, growth, differentiation, and apoptosis. The MYC gene is genetically activated and overexpressed in many human cancers and this overexpression has been causally linked to tumorigenesis. The host immune system generally serves as a barrier against tumor formation. Activation of the immune response can contribute to tumor regression with both adaptive and innate immune effectors. Programmed death-ligand 1 (or PD-L1, also known as CD274 and B7-H1) is a critical 'don't find me' signal to the adaptive immune system, whereas CD47 is a critical 'don't eat me' signal to the innate immune system as well as a regulator of the adaptive immune response. These and similar molecules are often overexpressed on human tumors. Recently, it was shown that MYC regulates the anti-tumor immune response through CD47 and PD-L1 (Casey et al. 2016). Therapeutic suppression of PD-L1 and other immune checkpoint molecules elicit immune responses against tumors.

Compositions

The present invention includes compositions comprising MYC mRNA antagonists that home in on cancer cells. One embodiment includes an antisense 2'-O,4'-C-aminomethylene-bridged nucleic acid (NC-BNA)-DNA-NC-BNA chimera (BNA), capable of knocking down MYC mRNA activity. The BNA comprises the sequence 5'-GCTGGAAT-TACTACA-3' (SEQ ID NO: 2). The BNA is capable of knocking down c-Myc protein expression. In addition, the BNA is capable of knocking down PD-L1, PD-L2, CD47, and JAK2 mRNA and/or protein expression.

In certain embodiments, the BNA further comprises a conjugated peptide capable of directing endocytosis via the insulin-like growth factor 1 (IGF1) receptor. For example, the BNA of the present invention can be covalently linked to a D(Cys-Ser-Lys-Cys) tetrapeptide analog IGF1 at the 5' or 3' end of the BNA via a spacer to direct endocytosis into cells that overexpress IGF1R (Basu and Wickstrom, 1997, Bioconjugate Chemistry 8(4):481-488). In certain embodiments, the conjugated peptide comprises the sequence: D(Cys-Ser-Lys-Cys) (SEQ ID NO: 3). In other embodiments, the peptide comprises the sequence D(Cys-Ser-Lys-Cys) (SEQ ID NO: 3) and the spacer aminoethoxyethoxyacetate (AEEA) (SEQ ID NO: 4) is replaced with a different linker. A wide variety of spacers are commonly utilized in the art of biochemical conjugates, including but not limited to alkyl (heptyl and hexyl) chains, and their click chemistry conjugates, such as alkyl-triazoyl-alkyl spacers.

The BNAs of the present invention can be part of a kit, which includes instructional material for use thereof. The BNAs can also be contained in a sterile vial or container. The BNAs can be GMP-produced and suitable for infusion after dissolving for example in sterile saline. The BNAs can also be part of a pharmaceutical composition comprising the BNA pharmaceutically acceptable carrier.

The compositions of the present invention should be construed to optionally encompass any modifications to the phosphate backbone linkages commonly known in the art. Nonexclusive examples of modifications contemplated for the phosphate backbone include boranophosphate, methylphosphonate, phosphorothioate, phosphoramidates, and the like. In the nucleic acid molecules of the invention, phosphorothioate, methylphosphonate, or boranophosphate modifications directly stabilize the internucleoside phosphate linkage. Boranophosphate modified RNAs are highly nuclease resistant, potent as silencing agents, and are relatively non-toxic. Boranophosphate DNAs are synthesized by an H-phosphonate route (U.S. Pat. No. 5,859,231). Boranophosphate modified RNAs cannot be manufactured using standard chemical synthesis methods and instead are made by in vitro transcription (IVT) (Hall et al., 2004 and Hall et al., 2006). Phosphorothioate and methylphosphonate modifications can be readily placed in a nucleic acid molecule of the invention at any desired position and can be made using standard chemical synthesis methods.

In RNA analogs, a variety of substitutions can be placed at the 2'-position of the ribose. Such 2' modifications generally increase duplex stability (Tm) and can greatly improve nuclease resistance. Examples of modifications contemplated for the ribose moiety include 2'-O-alkyl, such as 2'-O-methyl, 2'-fluoro, 2'-amino modifications and the like (see, e.g., Amarzguioui et al., 2003). Examples of replacements for ribose include arabinose, morpholine, acyclic sugars, and the like.

Locked nucleic acids (2'-O,4'-C-methylene bridged nucleic acids) (LNAs) are a particular class of ribose-modification that can be incorporated to stabilize nucleic acid molecules of the invention. Many other modifications are known and can be used so long as the above criteria are satisfied. Examples of modifications are also disclosed in U.S. Pat. Nos. 5,684,143, 5,858,988 and 6,291,438 and in U.S. published patent application No. 2004/0203145 A1. Other modifications are disclosed in Herdewijn (2000), Eckstein (2000), Rusckowski et al. (2000), Stein et al. (2001); Vorobjev et al. (2001). Peptide nucleic acids (PNAs) are chemically synthesized oligoamides of N-aminoethyl glycine with nucleic acid bases attached to the alpha amine of glycine (Nielsen, P. E., et al., 1991, Science 254(5037) 1497-1500, U.S. Pat. No. 5,539,082).

Modifications contemplated for the 1'-base groups include modified pyrimidines, modified purines, and the like.

Methods of Treatment

The invention also includes methods of treating a condition in a subject comprising administering to the subject a therapeutically effective amount of a BNA capable of blocking MYC mRNA expression. The BNA comprises SEQ ID NO: 2. The method can further comprise knocking down PD-L1 mRNA expression. The BNA can be conjugated with a peptide capable of directing endocytosis via the insulin-like growth factor 1 (IGF1) receptor. In certain embodiments, the conjugated peptide comprises the sequence: D(Cys-Ser-Lys-Cys) (SEQ ID NO: 3). In other embodiments, the peptide comprises the sequence D(Cys-Ser-Lys-Cys) (SEQ ID NO: 3) and the spacer sequence AEEA (SEQ ID NO: 4).

In certain embodiments, the condition to be treated by the methods of the present invention is cancer. In certain embodiments the type of cancer to be treated is lung cancer or breast cancer. However, any type of cancer known in the art can be treated by the methods of the present invention, including but not limited to, carcinoma, lymphoma, blastoma, sarcoma, leukemia, lymphoid malignancies, kidney cancer, renal cancer, breast cancer, colon cancer, rectal cancer, colorectal cancer, lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, liver cancer, bladder cancer, cancer of the peritoneum, hepatocellular cancer, gastric or stomach cancer including gastrointestinal cancer, gastrointestinal stromal tumors (GIST), pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulvar cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, urinary tract carcinomas, thyroid carcinomas, Wilm's tumor, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia, chronic myeloblastic leukemia; and post-transplant lymphoproliferative disorder (PTLD), as well as abnormal vascular proliferation associated with phakomatoses, edema (such as that associated with brain tumors), and Meigs' syndrome. "Tumor", as used herein, refers to all neoplastic cell growth and proliferation, whether malignant or benign, and all pre-cancerous and cancerous cells and tissues.

In the context of treatment for cancer, the compositions of the present invention can optionally be administered to a patient in combination with other chemotherapeutic agents, molecularly targeted inhibitors, therapeutic antibodies, or gene therapies. Suitable chemotherapeutic agents include, for example, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins, capecitabine; and pharmaceutically acceptable salts, acids or derivatives of any of the above. Additional information on the methods of cancer treatment is provided in U.S. Pat. No. 7,285,522, incorporated by reference in its entirety.

Additionally, the methods of the present invention are capable of treating other conditions wherein reduction of MYC activity is beneficial. Such conditions include but are not limited to inflammatory disorders, such as arthritis, neurological disorders, cardiovascular disorders, and autoimmune disorders.

The invention also includes methods of knocking down MYC mRNA expression in a cell. In one embodiment, the method comprises contacting the cell with a BNA comprising SEQ ID NO: 2. By knocking down MYC mRNA translation, it would follow that c-Myc protein expression can also be knocked down in a cell by the methods described herein. In certain embodiments, knocking down MYC mRNA translation further comprises knocking down PD-L1 mRNA and/or protein expression. The BNA used in the methods can further comprise a conjugated peptide capable of directing endocytosis via the insulin-like growth factor 1 (IGF1) receptor. In one embodiment, the peptide comprises SEQ ID NO: 3. In another embodiment, the peptide comprises SEQ ID NO: 3 and SEQ ID NO: 4.

Pharmaceutical Compositions and Formulations

The invention also encompasses the use of a pharmaceutical composition of the invention to practice the methods of the invention. Such a pharmaceutical composition may be provided in a form suitable for administration to a subject, and may be comprise one or more pharmaceutically acceptable carriers, one or more additional ingredients, or some combination of these. The at least one composition of the invention may comprise a physiologically acceptable salt, such as a compound contemplated within the invention in combination with a physiologically acceptable cation or anion, as is well known in the art.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In one embodiment, the compositions of the invention are formulated using one or more pharmaceutically acceptable excipients or carriers. In one embodiment, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Animal Cell Culture" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting" (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, practice the claimed methods of the present invention. The following working examples therefore, specifically point out the exemplary embodiments of the present invention, and are not to be construed as limiting in any way the remainder of the disclosure.

Example 1

Previous work on nucleic acid thermodynamics revealed that complementary 12-15 nucleotide DNA analogs bind strongly enough to oncogene mRNAs to specifically knock down MYC mRNA translation. Solid phase methods to synthesize oligonucleotides resulted in the generation of anti-MYC 15mer DNA analogs. Their knockdown efficacy was determined in human in cancer cells (Wickstrom et al., *Proceedings of the National Academy of Sciences* 85.4 (1988): 1028-1032, Wickstrom et al., *In vitro cellular & developmental biology* 25.3 (1989): 297-302, Bacon and Wickstrom, *Oncogene research* 6.1 (1991): 13-19., Bacon and Wickstrom, *Oncogene research* 6.1 (1991): 21-32) and animal tumors (Wickstrom et al., *Cancer research* 52.24 (1992): 6741-6745., Huang et al. 1995 *Molecular Medicine* 1.6 (1995): 647-658, Smith and Wickstrom, *Journal of the National Cancer Institute* 90.15 (1998): 1146-1154.). Therapeutic antisense oligonucleotides are currently being developed and entering the clinic.

Recently, the potential for MYC knockdown to reactivate immune surveillance of cancer cells (Casey et al., *Science* 352:6282 (2016): 227-231) led to the re-examination of the MYC mRNA 5'-untranslated region for additional, unexpected sites for antisense knockdown. A sequence was chosen corresponding to the 5' end of the secondary, shorter transcript of MYC mRNA (Hann et al. *Cell* 52.2 (1988): 185-195) at nt 170-184 of NCBI Reference Sequence NM_002467.4 REF, 5'-rUGUAGUAAUUCCAGC-3' (SEQ ID NO: 1). The novel antisense sequence was prepared as a 5-5-5 gapmer of NC-BNA (Rahman et al. *J Am Chem Soc* 130.14 (2008): 4886-4896), DNA, and NC-BNA: 5'-GCTG-GAATTACTACA-3', referred to herein as a "BNA" (SEQ ID NO: 2).

Figure 1B:
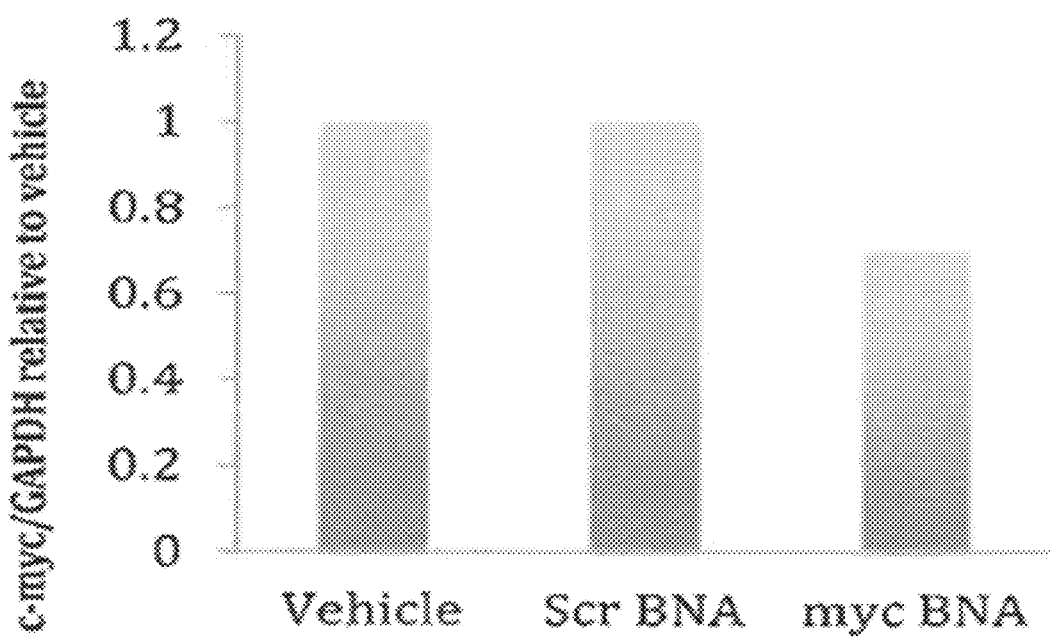
Figure 1C:
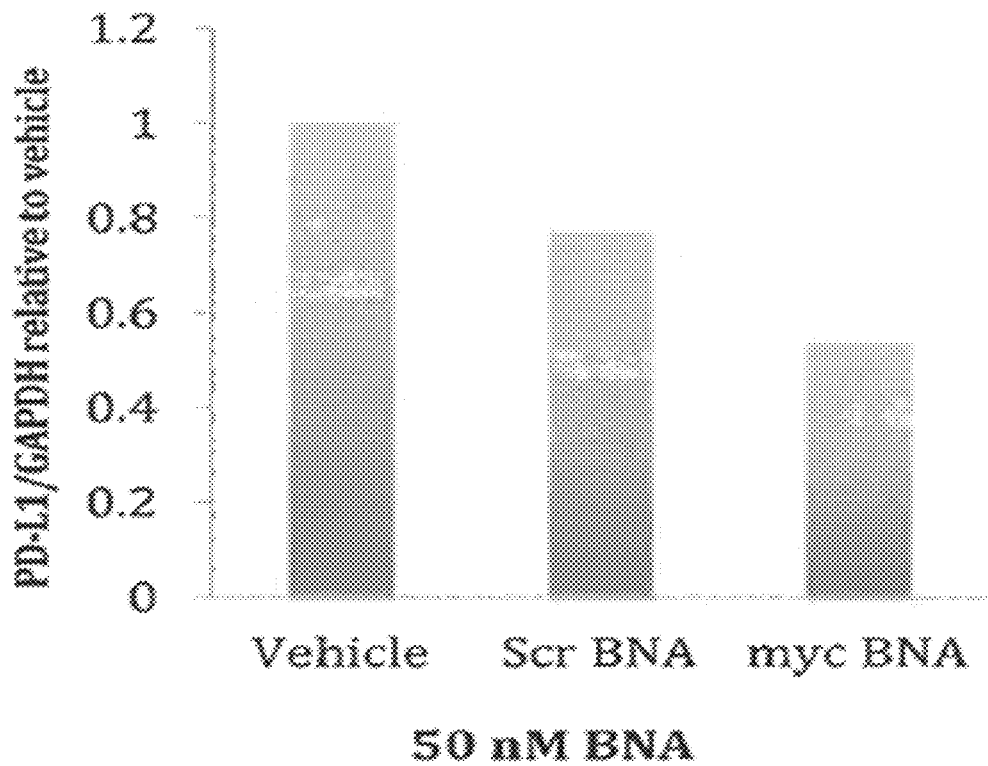
Figure 2:
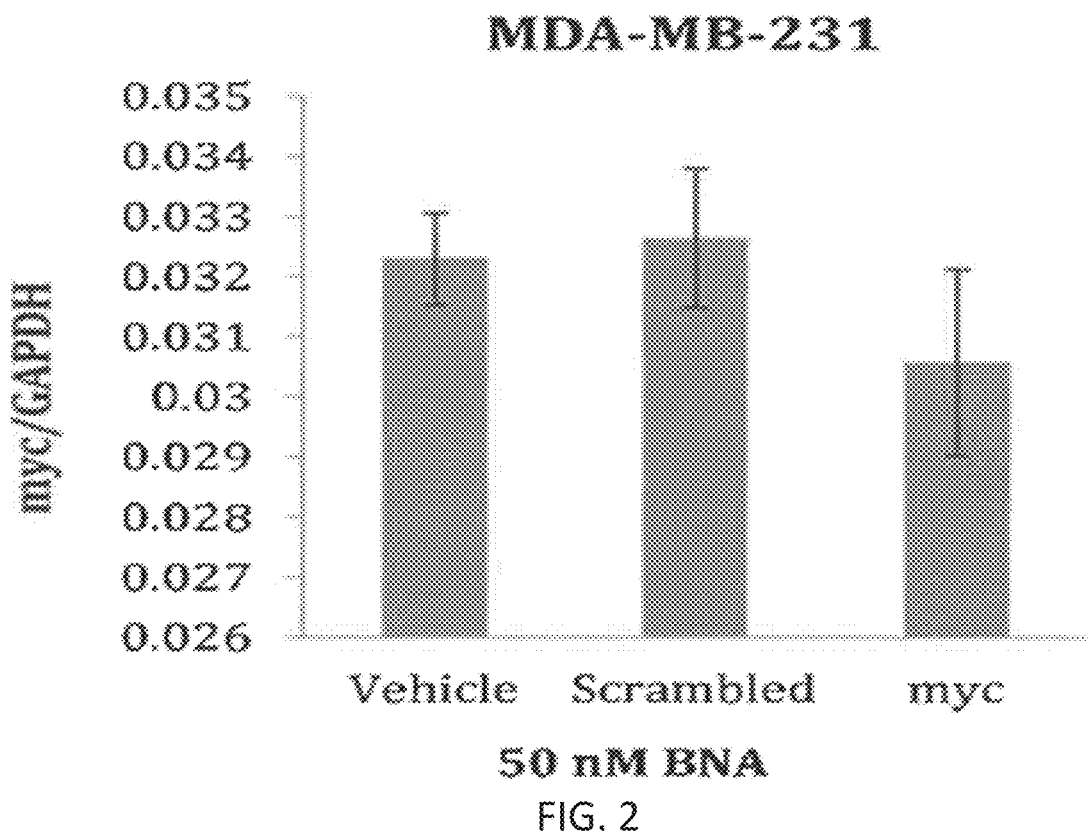
FIG. 2 is a graph illustrating the MYC BNA effect on the expression of MYC mRNA. Transfection of 50 nM MYC BNA in MDA-MB-231 cells modulated the amount of MYC mRNA 24 hour post transfection. n=6; error bar=SEM.
Figure 3A:
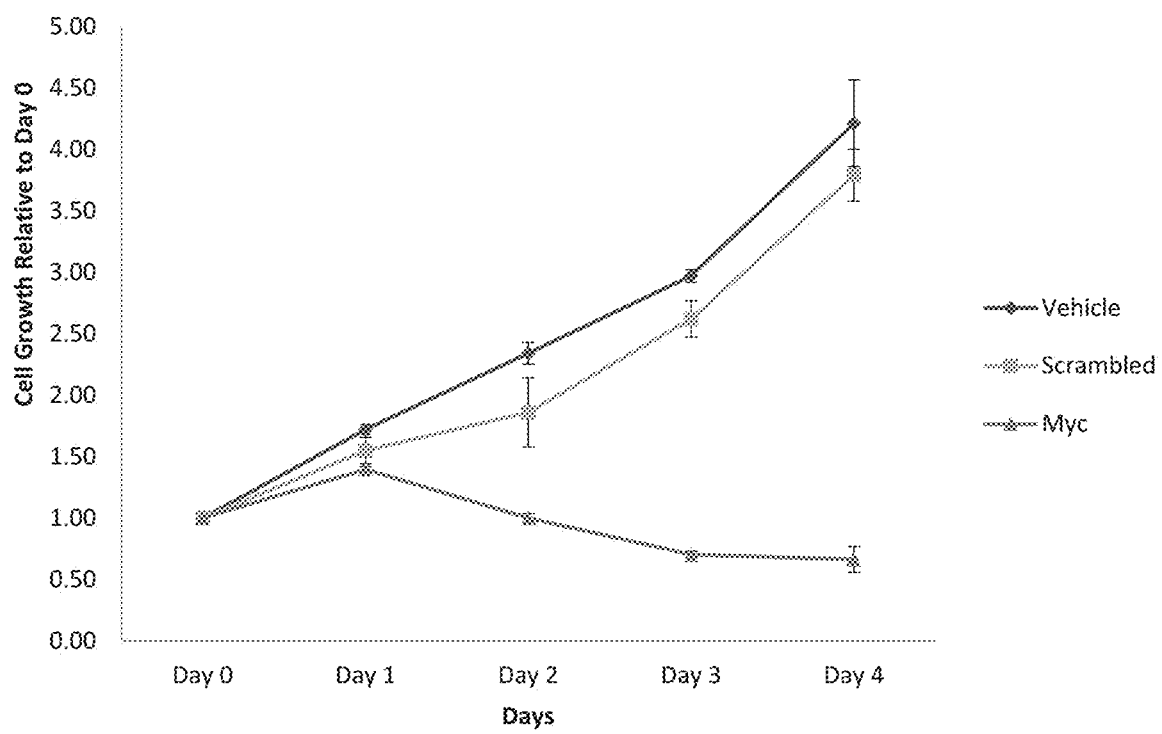
FIGS. 3A-3I are a series of graphs illustrating results from cell proliferation assays from triple negative breast cancer cells (FIGS. 3A-3H) and lung cancer cells (FIG. 3I) transfected with 50 nM of MYC BNA. n=3; Error bar, SD.
Figure 3B:
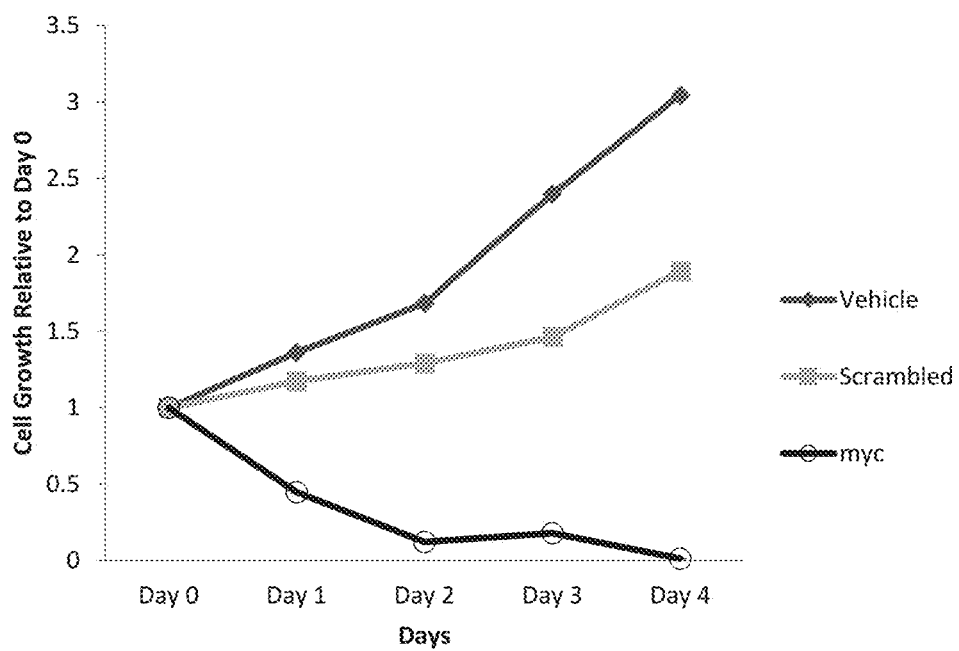
Figure 3C:
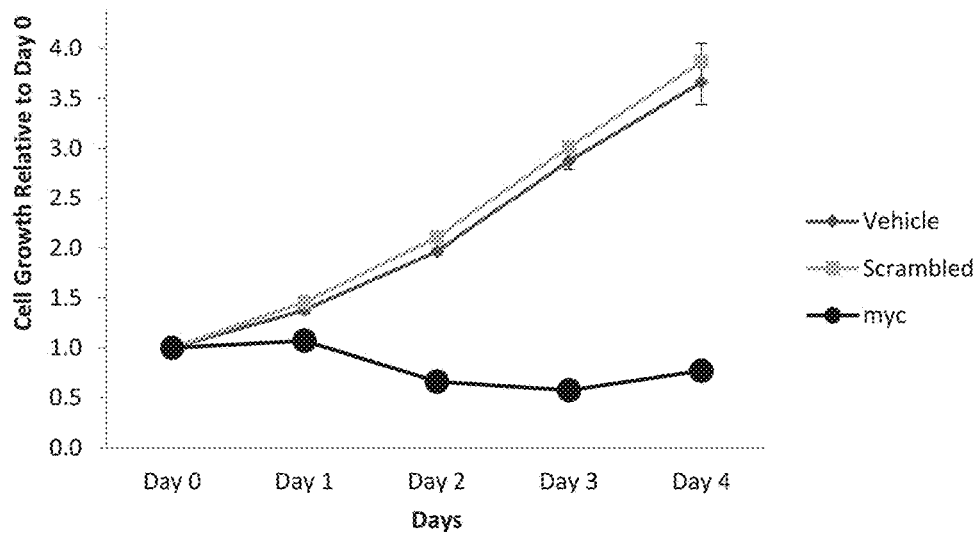
Figure 3D:
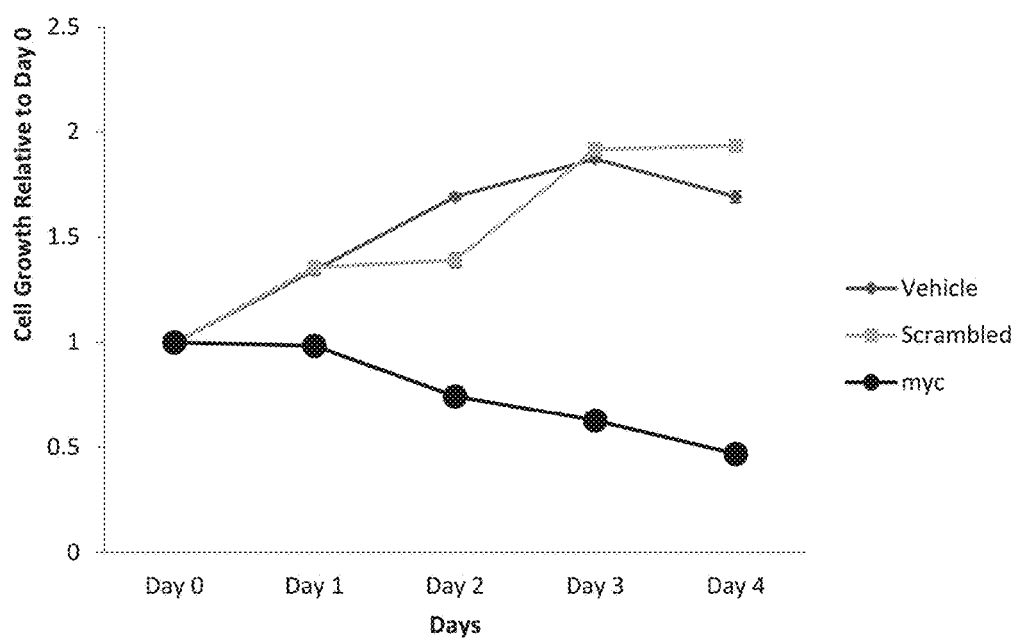
Figure 3E:
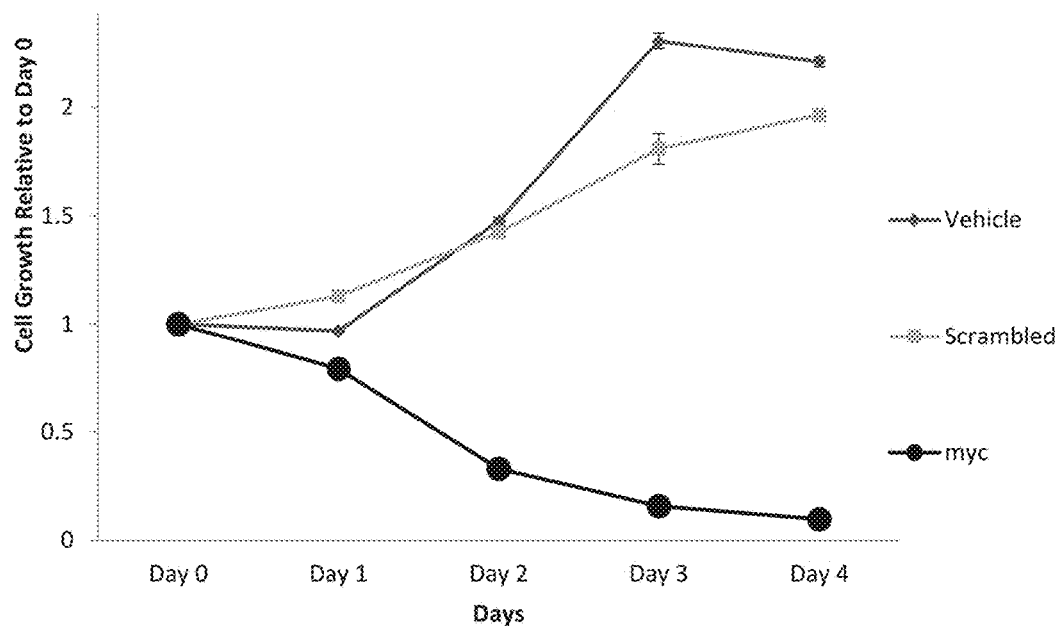
Figure 3F:
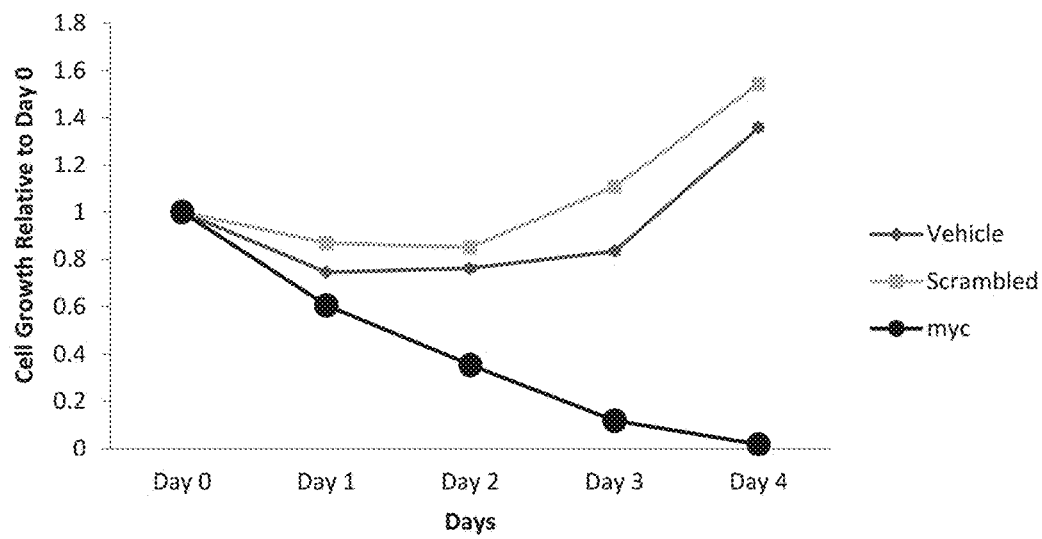
Figure 3G:
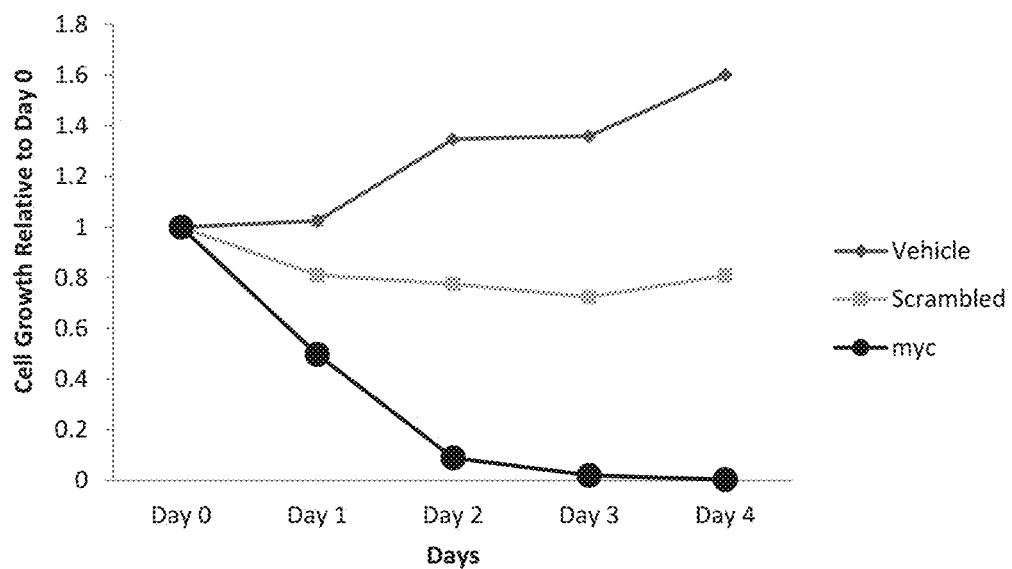
Figure 3H:
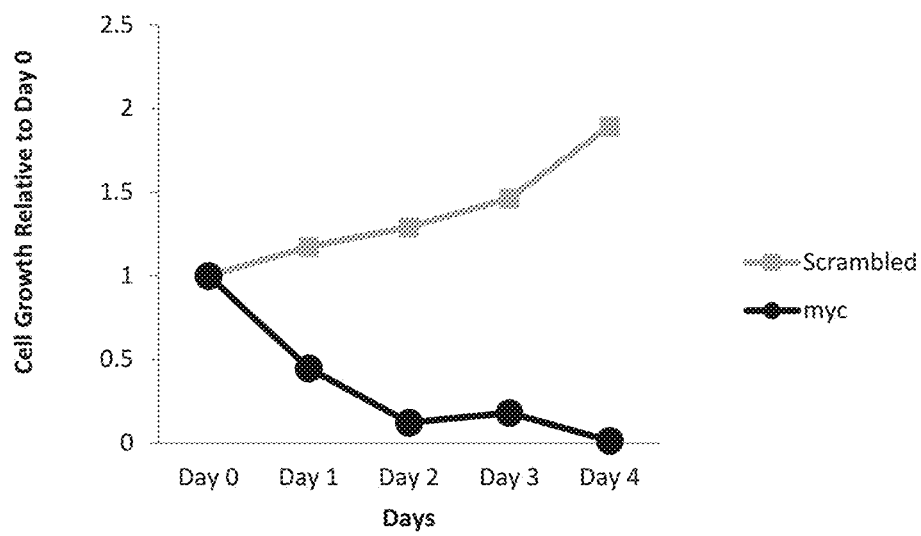
Figure 3I:
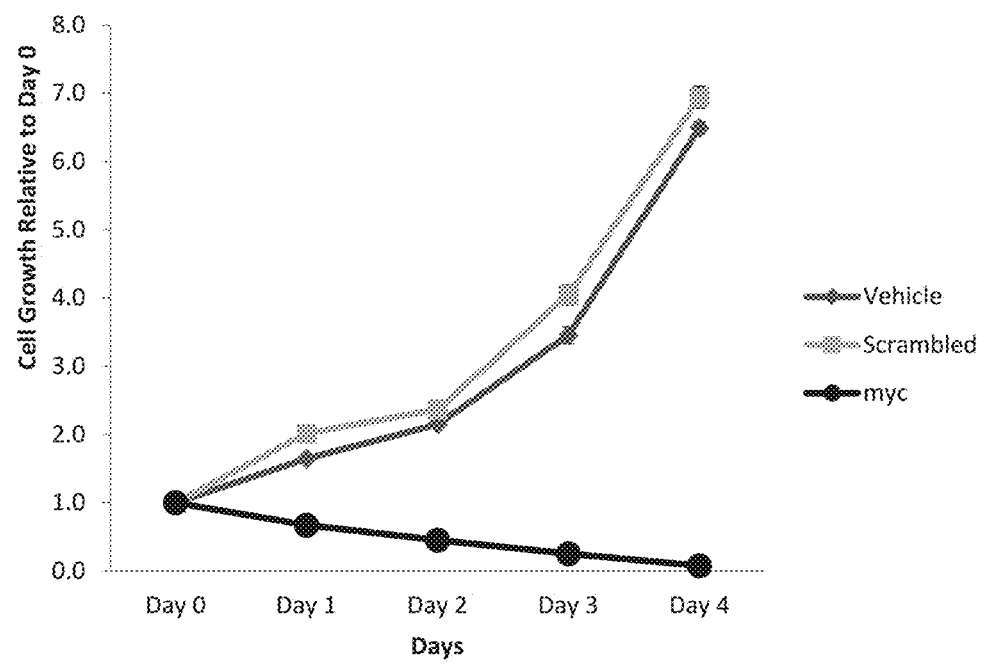

The anti-MYC 15mer (MYC BNA) was transfected into breast cancer and lung cancer cells and suppressed cancer cell proliferation and immune checkpoint cell surface protein PD-L1 at nM concentrations. Transfection of only 50 nM MYC BNA into MDA-MB-231 cells lowered c-Myc and PD-L1 protein expression within 48 hours post transfection (FIGS. 1A-1C). Transfection of 50 nM MYC BNA in MDA-MB-231 cells also modulated the amount of MYC mRNA within 24 hours post transfection (FIG. 2). Triple negative breast cancer cells (FIGS. 3A-3H) and lung cancer cells (FIG. 3I) were transfected with 50 nM of MYC BNA, then cell proliferation assays performed. Results showed a pronounced decrease in proliferation in all cell lines transfected with MYC BNA.

A further analog of 5'-GCTGG.AATTA.CTACA-3' (SEQ ID NO: 2) is evaluated that includes a conjugated peptide to direct endocytosis via the IGF1 receptor, without the need for transfection or any formulation agent. In one embodiment, the D(Cys-Ser-Lys-Cys) (SEQ-ID NO: 3) tetrapeptide analog of insulin-like growth factor 1 (IGF1) is covalently linked via a spacer to the 5' or 3' terminus of MYC BNA to direct endocytosis into cells that overexpress IGF1R (Basu and Wickstrom, 1997, *Bioconjugate Chemistry* 8(4):481-488). In one embodiment, the spacer comprises the sequence AEEA (SEQ ID NO: 4). In another embodiment, the spacer can be replaced with any other linker known in the art, among which are alkyl (heptyl and hexyl) chains, and their click chemistry conjugates, such as alkyl-triazoyl-alkyl spacers.

The MYC BNA coupled with the peptide is tested for cellular uptake, receptor mediated endocytosis, cellular proliferation, reduction in c-Myc protein, knockdown of MYC mRNA, apoptosis, migration, invasion, immune checkpoint marker reduction, and immune response.

Example 2

Figure 4:
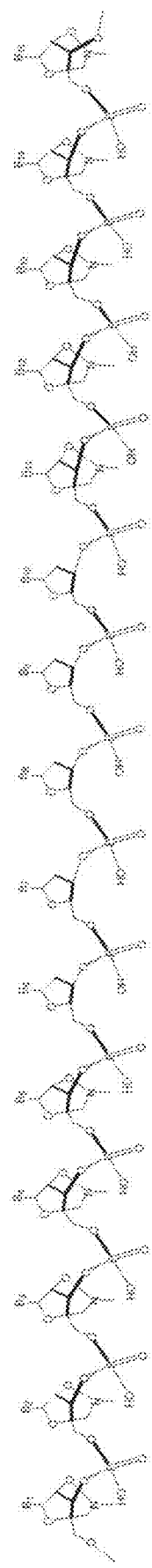
FIG. 4 depicts a schematic of an embodiment of the BNA-DNA-BNA for transfection.
Figure 5:
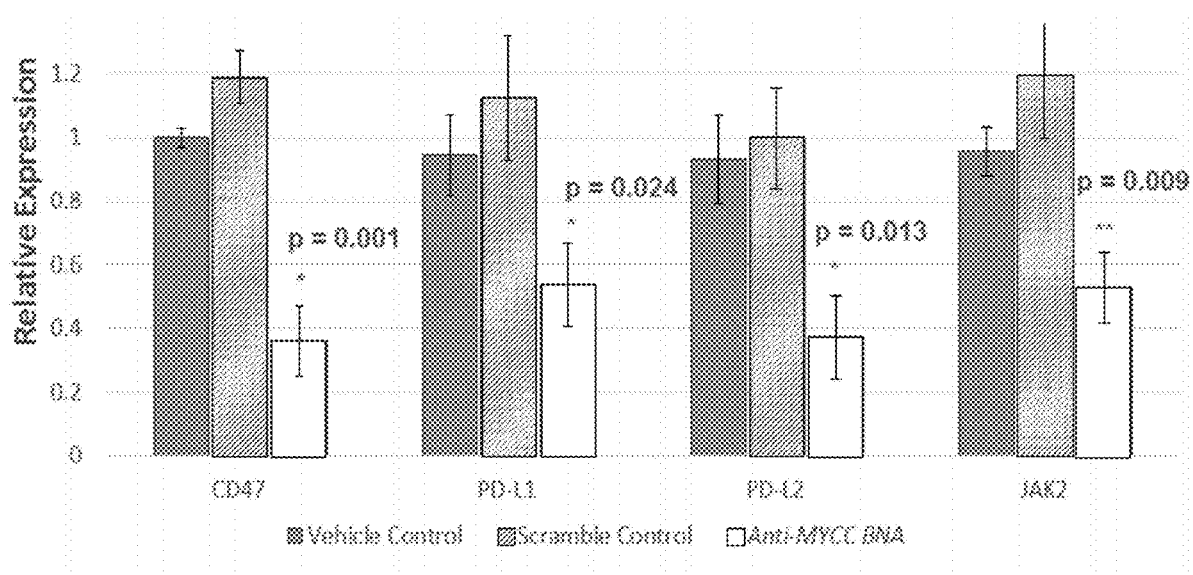
FIG. 5 depicts the effects of MYC blockade on mRNA levels of CD47, PD-L1, PD-L2, and JAK2 mRNA extracted from MDA-MB-231 cells transfected with scrambled control BNA or MYC BNA was analyzed by qPCR. Data are expressed as relative expression to GAPDH (mean±SEM) to the vehicle control and represent three biological triplicates. [*=p<0.05, **=p≤0.01 vs. scrambled control; one way t-test].

MYC blocker caused reduction of immune checkpoint mRNAs: CD47, PD-L1, PD-L2, and JAK2 mRNA extracted from MDA-MB-231 cells transfected with 50 nM scrambled control BNA or 50 nMMYC BNA (FIG. 4) were quantitated by qPCR, relative to GAPDH. A short MYC BNA blocker designed according to the invention as described herein significantly reduced mRNA levels of PD-L1 and PD-L2 ($p<0.05$) and drastically reduced mRNA levels of CD47 and JAK2 ($p<0.01$) (FIG. 5).

Figure 6:
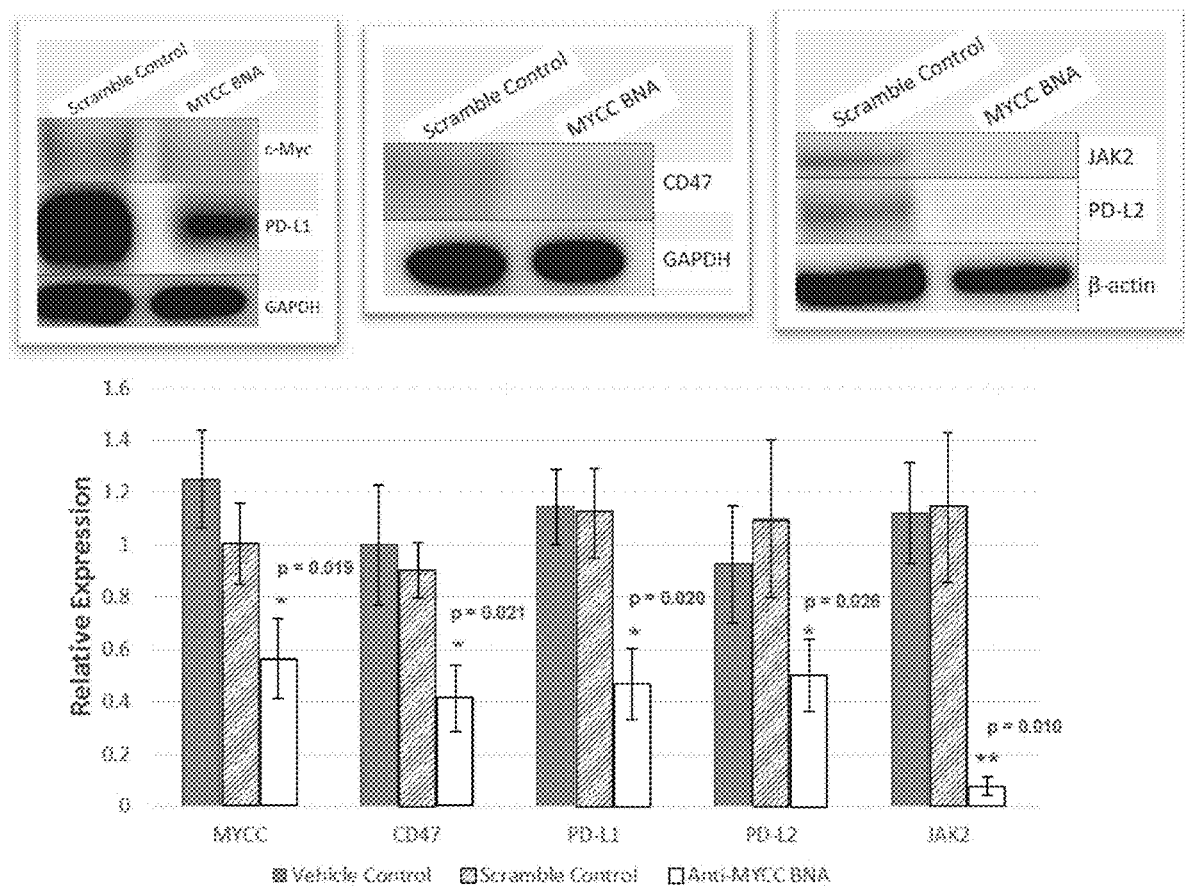
FIG. 6 depicts the effects of MYC blockade on cytoplasmic protein levels of c-Myc, CD47, PD-L1, PD-L2, and Jak2. Proteins extracted from MDA-MB-231 cells transfected with scrambled control BNA or MYC BNA were analyzed by Western blot, normalized against GAPDH. Data are expressed as relative expression (mean±SEM) to the vehicle control and represent three individual experiments. [*=p<0.05 vs. scrambled control; one way t-test]. Top: representative images. Bottom: bar graph quantitation.

MYC blocker caused reduction of immune checkpoint proteins: c-Myc, CD47, PD-L1, PD-L2, and Jak2 proteins extracted from MDA-MB-231 cells transfected with 50 nM scrambled control BNA or 50 nMMYC BNA were quantitated by Western blot, relative to GAPDH. The lysis method for this experiment was chosen to extract cytoplasmic proteins, but not membrane-bound cell surface proteins. Thus, the results reflect the effect of MYC blockade on cytoplasmic expression of new membrane proteins in transit. Short MYC BNA blockers designed according to the invention as described herein significantly reduced c-Myc, CD47, PD-L1, PD-L2 cytoplasmic protein levels ($p<0.05$), and dramatically reduced Jak2 protein levels ($p=0.01$) (FIG. 6).

Figure 7:
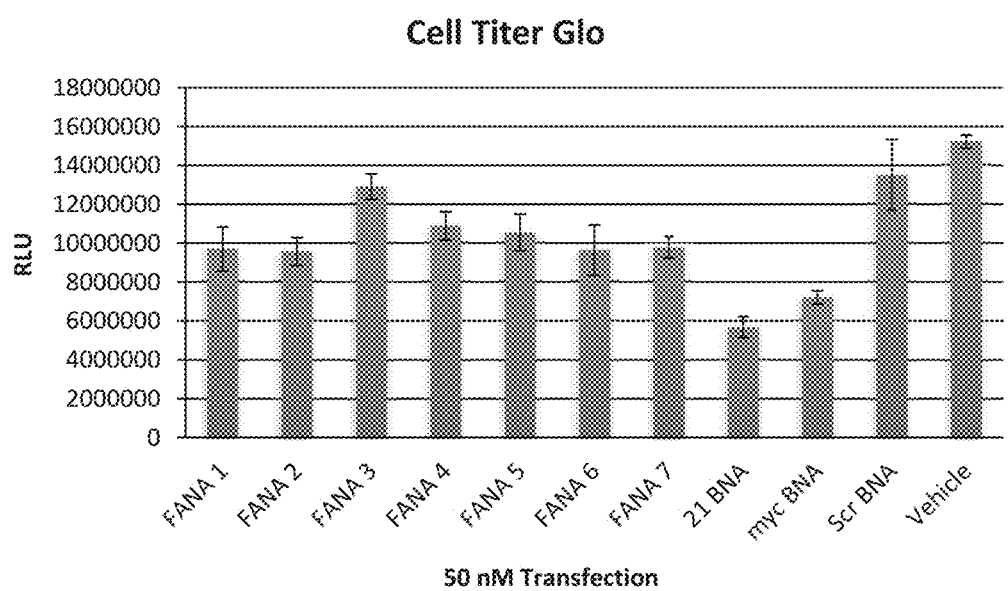
FIG. 7 depicts the effects of MYC blockade on proliferation of MDA-MB-231 cells transfected with 2' fluoro-arabino nucleic acid (FANA) vs. BNA, for 2 days, analyzed by ATP content of lysed cells. Data are expressed as relative expression (mean±SD) to the vehicle control and represent three individual experiments. [*=p<0.05 vs. scrambled control; one way t-test].

While BNA MYC blocker caused reduction of TNBC cell growth, FANA equivalent failed: Proliferation of MDA-MB-231 cells transfected with 50 nMMYC BNA or controls, compared with MYC 2' fluoro-arabino nucleic acid (FANA) (Mangos, M. M. et al., J Am Chem Soc 125(3): 654-61 (2003) PMID: 12526664) or controls, was analyzed by luciferase detection of ATP in cell lysates over 2 days. Proliferation of MDA-MB-231 cells was significantly ($p<0.05$) inhibited by MYC BNA blocker, while the MYC FANA 6 sequence, and other FANA controls, did not show significant slowing of cell proliferation when compared to BNA (FIG. 7). Thus, the novel MYC BNA antisense agent was significantly more efficacious than the MYC FANA antisense agent.

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A 2'-O, 4'-C-aminomethylene bridged nucleic acid (BNA)-deoxyribonucleic acid (DNA)-2'O, 4'-C-aminomethylene bridged nucleic acid (BNA) chimeric antisense oligonucleotide for reduction of MYC activity, wherein the BNA-DNA-BNA chimeric antisense oligonucleotide comprises SEQ ID NO: 2.

2. The BNA-DNA-BNA chimeric antisense oligonucleotide of claim 1, wherein the DNA comprises a modified backbone linkage selected from at least one of a boranophosphate, methylphosphonate, phosphorothioate, and phosphoramidates backbone linkage.

3. The BNA-DNA-BNA chimeric anti sense oligonucleotide of claim 2, further comprising a conjugated peptide which undergoes endocytosis via the insulin-like growth factor 1 (IGF1) receptor.

4. The BNA-DNA-BNA chimeric anti sense oligonucleotide of claim 3, wherein the peptide comprises SEQ ID NO: 3.

5. A pharmaceutical composition comprising the BNA-DNA-BNA chimeric antisense oligonucleotide of claim 1 and a pharmaceutically acceptable carrier.

6. A kit comprising a 2'-O, 4'-C-aminomethylene bridged nucleic acid (BNA)-deoxyribonucleic acid (DNA)-2'O, 4'-C-aminomethylene bridged nucleic acid (BNA) chimeric antisense oligonucleotide which reduces MYC activity, wherein the BNA-DNA-BNA chimeric anti sense oligonucleotide comprises SEQ ID NO: 2, and instructional material for use thereof.

7. The kit of claim 6, wherein said deoxynucleic acid (DNA) comprises a backbone modification selected from at least one of a boranophosphate, methylphosphonate, phosphorothioate, and phosphoramidates backbone linkage.

8. A method for reducing MYC mRNA translation in a cell, the method comprising contacting the cell with a 2'-O, 4'-C-aminomethylene bridged nucleic acid (BNA)-deoxyribonucleic acid (DNA)-2'O, 4'-C-aminomethylene bridged nucleic acid (BNA) chimeric antisense oligonucleotide comprising SEQ ID NO: 2.

9. The method of claim 8, wherein reduction of MYC mRNA translation causes a reduction in PD-L1 protein expression.

10. The method of claim 8, wherein the BNA-DNA-BNA chimeric antisense oligonucleotide further comprises a conjugated peoptide which undergoes endocytosis via the insulin-like growth factor 1 (IGF1) receptor.

11. The method of claim 10, wherein the peptide comprises SEQ ID NO: 3.

12. The method of claim 8, wherein reduction of MYC mRNA translation causes a reduction in PD-L2, CD47, and Jak2 protein expression.

13. A method of treating a condition in a subject, the method comprising administering to the subject a therapeutically effective amount of a 2'-O, 4'-C-aminomethylene bridged nucleic acid (BNA)-deoxyribonucleic acid (DNA)-2'O, 4'-C-aminomethylene bridged nucleic acid (BNA) chimeric antisense oligonucleotide for reducing MYC mRNA translation, wherein the BNA-DNA-BNA chimeric antisense oligonucleotide comprises SEQ ID NO: 2.

14. The method of claim 13, wherein reduction in MYC mRNA translation causes a reduction in PD-L1 protein expression.

15. The method of claim 13, wherein the BNA-DNA-BNA chimeric antisense oligonucleotide further comprises a conjugated peptide which undergoes endocytosis via the insulin-like growth factor 1 (IGF1) receptor.

16. The method of claim 15, wherein the peptide comprises SEQ ID NO: 3.

17. The method of claim 13, wherein the condition is cancer.

18. The method of claim 17, wherein the cancer is selected from the group consisting of breast cancer and lung cancer.

19. The method of claim 13, wherein the condition is selected from the group consisting of inflammation, arthritis, neurodegeneration, cardiovascular disease, and autoimmune disorders.

20. The method of claim 13, wherein reduction of MYC mRNA translation causes a reduction in PD-L2, CD47, and Jak2 protein expression.

21. The method of claim 13, wherein said deoxynucleic acid (DNA) comprises a backbone modification selected from at least one of a boranophosphate, methylphosphonate, phosphorothioate, and phosphoramidates backbone linkage.

* * * * *